United States Patent
Fukuhara et al.

(10) Patent No.: US 11,931,448 B2
(45) Date of Patent: Mar. 19, 2024

(54) WATER-IN-OIL TYPE EMULSION COMPOSITION

(71) Applicant: Shiseido Company, Ltd., Tokyo (JP)

(72) Inventors: Ryushi Fukuhara, Tokyo (JP); Yuki Sugiyama, Tokyo (JP); Takumi Watanabe, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 600 days.

(21) Appl. No.: 17/283,692

(22) PCT Filed: Oct. 7, 2019

(86) PCT No.: PCT/JP2019/039459
§ 371 (c)(1),
(2) Date: Apr. 8, 2021

(87) PCT Pub. No.: WO2020/075666
PCT Pub. Date: Apr. 16, 2020

(65) Prior Publication Data
US 2021/0346273 A1     Nov. 11, 2021

(30) Foreign Application Priority Data
Oct. 9, 2018  (JP) ................. 2018-190665

(51) Int. Cl.
| *A61K 8/81* | (2006.01) |
| *A61K 8/04* | (2006.01) |
| *A61K 8/894* | (2006.01) |
| *A61Q 1/02* | (2006.01) |
| *A61Q 19/00* | (2006.01) |

(52) U.S. Cl.
CPC ............ *A61K 8/894* (2013.01); *A61K 8/8147* (2013.01); *A61K 8/8164* (2013.01); *A61Q 19/00* (2013.01)

(58) Field of Classification Search
None
See application file for complete search history.

(56) References Cited

U.S. PATENT DOCUMENTS

| 2014/0193471 A1 | 7/2014 | Lemoine et al. |
| 2014/0343170 A1 | 11/2014 | Sugiyama et al. |
| 2017/0239165 A1 | 8/2017 | Sugiyama et al. |
| 2018/0028416 A1 | 2/2018 | Fu et al. |
| 2019/0290572 A1* | 9/2019 | Sugiyama ............. A61K 8/06 |
| 2021/0330573 A1 | 10/2021 | Sugiyama et al. |

FOREIGN PATENT DOCUMENTS

| JP | 2005-015623 A | 1/2005 |
| JP | 2006-161026 A | 6/2006 |
| JP | 2006-161027 A | 6/2006 |
| JP | 2007-106694 A | 4/2007 |
| JP | 2007-126394 A | 5/2007 |
| JP | 2007-238521 A | 9/2007 |
| JP | 4577721 B2 | 11/2010 |
| JP | 5207424 B1 | 6/2013 |
| JP | 2017-175011 A | 9/2017 |
| JP | 2018-070554 A | 5/2018 |
| WO | WO-2016/021338 A1 | 2/2016 |
| WO | WO-2018/061755 A1 | 4/2018 |

\* cited by examiner

*Primary Examiner* — Brian Gulledge
(74) *Attorney, Agent, or Firm* — Foley & Lardner LLP

(57) ABSTRACT

A water-in-oil emulsion composition that is significantly excellent in emulsification stability, and also excellent in non-stickiness is provided. The water-in-oil emulsion composition includes (a) a polyoxyalkylene/alkyl co-modified silicone; (b) a core-corona particle; (c) an oil-phase component; and (d) an aqueous-phase component.

4 Claims, No Drawings

WATER-IN-OIL TYPE EMULSION COMPOSITION

RELATED APPLICATION

This application is the U.S. National Stage of PCT/JP2019/039459, filed Oct. 7, 2019, which claims the priority to Japanese Patent Application No. 2018-190665, filed on Oct. 9, 2018, the disclosure of which is incorporated herein by reference in its entirety.

FIELD OF THE INVENTION

The present invention relates to a water-in-oil emulsion composition, and more specifically to a water-in-oil emulsion composition obtained by emulsifying a core-corona particle and a specific lipophilic surfactant.

BACKGROUND OF THE INVENTION

In recent years, polymeric microparticles having various characteristics have been produced, and are widely used in fields of pharmaceuticals and cosmetics. Polymeric microparticles are produced by heterogeneous polymerization methods such as a microemulsion polymerization method, and are classified into several types by their compositions and forms.

A core-corona particle that is one of them is developed by the present inventors (Patent Literatures 1, 7). It has a spherical body consisting of a polymer of which a hydrophilic group is graft-bonded to a hydrophobic polymer skeleton, and has a structure of which a corona part consisting of a hydrophilic group is disposed around a hydrophobic center part (core part).

The core-corona particle is used as an emulsifier for producing an oil-in-water emulsion composition since it can stably disperse in water by hydrophilicity of the corona part (e.g., Patent Literatures 2, 7), although the core part of the core-corona particle has an excellent affinity to organic solvents. Pickering emulsion is known as an oil-in-water emulsified particle using a powder as an emulsifier, and the emulsified particles easily coalesce by stirring or impact; whereas, the oil-in-water emulsified particles emulsified by the core-corona particles are significantly stable to physical impacts. Moreover, in general, although the emulsion system obtained by emulsifying with a surfactant is greatly affected by temperature, an emulsion system obtained by the core-corona particle is hardly affected by temperature change.

Furthermore, the core-corona particle is known to be capable of being used as a clouding agent for clouding cosmetics (Patent Literature 3), and a capsule agent using swelling ability exhibited by organic solvents (Patent Literatures 4, 5).

As describe above, the core-corona particles were widely known in applications as emulsifiers that generate oil-in-water emulsion systems (e.g., Patent Literatures 2, 7), clouding agents of aqueous systems (Patent Literature 3), and inclusion complexes for blending slightly water-soluble components to aqueous systems (Patent Literature 4).

CITATION LIST

Patent Literatures

PATENT LITERATURE 1: Japanese Unexamined Patent Publication No. 2005-015623A
PATENT LITERATURE 2: Japanese Patent No. 5207424B
PATENT LITERATURE 3: Japanese Patent No. 4577721B
PATENT LITERATURE 4: Japanese Unexamined Patent Publication No. 2007-238521A
PATENT LITERATURE 5: Japanese Unexamined Patent Publication No. 2006-161026A
PATENT LITERATURE 6: Japanese Unexamined Patent Publication No. 2006-161027A
PATENT LITERATURE 7: Japanese Unexamined Patent Publication No. 2017-175011A

DISCLOSURE OF THE INVENTION

Technical Problem

The emulsion compositions that are emulsified by surfactants generally have a problem of stickiness that occurs when the blending amount of the surfactant is increased in order to improve emulsification stability, and thus feeling of use deteriorates. This problem was more serious for the water-in-oil emulsion composition having an oil phase as the continuous phase than the oil-in-water emulsion composition having an aqueous phase as the continuous phase. This is because the oil-in-water emulsion composition having the aqueous phase as the continuous phase can gain contribution of stabilization such as hydration repulsion between emulsified particles or electric double-layer ability; whereas, the water-in-oil emulsion composition cannot gain such contribution of stabilization, and the oil-water interface film needs to be strengthened by blending a large amount of a high-molecular weight surfactant having stronger stickiness, and stabilization of emulsified particles needs to be secured.

The present invention has been made for the problem of the above-described water-in-oil emulsion composition, and the object thereof is to provide a water-in-oil emulsion composition that is significantly excellent in emulsification stability and excellent in non-stickiness.

Solution to Problem

The present inventors have diligently studied the above-described problem, and as a result, they have surprisingly found that a core-corona microparticle that is known to produce a stable oil-in-water emulsion system produces a significantly stable water-in-oil emulsion system under coexistence with a specific oil-soluble surfactant. Furthermore, they have also found that a water-in-oil emulsion composition obtained with the core-corona particle is excellent in non-stickiness, and completed the present invention.

That is, the present invention comprises the following.

[1] A water-in-oil emulsion composition comprising:
(a) 0.5 to 3% by mass of a polyoxyalkylene/alkyl co-modified silicone;
(b) 0.01% by mass or greater of a core-corona particle;
(c) an oil-phase component; and
(d) an aqueous-phase component, wherein the core-corona particle (b) is obtained by radically polymerizing a polyethylene oxide macromonomer represented by the following formula (1), and a hydrophobic monomer selected from a group consisting of an acrylate/methacrylate derivative monomer represented by the following formula (2) and an acrylamide/methacrylamide derivative monomer represented by the following formula (3), under presence or absence of a crosslinking polymer represented by the following formula (4) and under the following conditions (A) to (E);

(A) a mole ratio expressed by a feed mole amount of the polyethylene oxide macromonomer/a feed mole amount of the hydrophobic monomer is 1:10 to 1:250;
(B) a feed amount of the crosslinking monomer relative to a feed amount of the hydrophobic monomer is 0.1 to 1.5% by mass;
(C) the acrylate/methacrylate derivative monomer represented by the following formula (2) has a monomer composition of which one type or two or more types of a methacrylic acid derivative having a 1-8C alkyl group is mixed; and
the acrylamide/methacylamide derivative monomer represented by the following formula (3) is an acrylamide derivative or a methacrylamide derivative having a substituent having a 1-18C alkyl group;
(D) a polymerization solvent is a water-alcohol mixed solvent, and the alcohol is one type or two or more types selected from a group consisting of ethanol, dipropylene glycol, 1,3-butylene glycol, and isoprene glycol; and
(E) solvent composition of the water-alcohol mixed solvent is water:alcohol=90 to 10:10 to 90 in a mass ratio at 20° C.

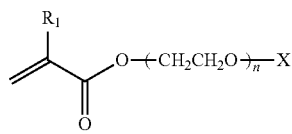

[Chem. 1]

(1) $R_1$ is H or a 1-3C alkyl group, and n is a number of 8 to 200. X is H or $CH_3$.

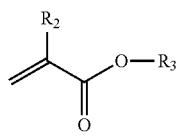

[Chem. 2]

(2) $R_2$ is a 1-3C alkyl group, and $R_3$ is a 1-12C alkyl group.

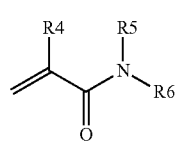

[Chem. 3]

(3) $R_4$ is H or a 1-3C alkyl group, and $R_5$ and $R_6$ are H or substituents having a 1-18C alkyl group.

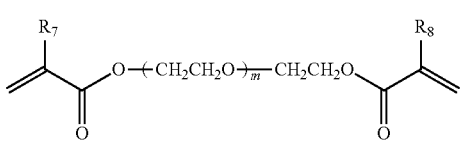

[Chem. 4]

(4) $R_7$ and $R_8$ are independently a 1-3C alkyl group, and m is a number of 0 to 2.

[2] The water-in-oil emulsion composition of [1], wherein the component (a) is one type or two or more types of a polyoxy alkylene/alkyl co-modified silicone selected from a group consisting of cetyl PEG/PPG-10/1 dimethicone and lauryl PEG-9 polydimethylsiloxyethyl dimethicone.

[3] The water-in-oil emulsion composition of [1] or [2], wherein 20 to 80% by mass of the oil-phase component (c) is comprised.

Effects of Invention

A water-in-oil emulsion composition that is significantly excellent in emulsification stability and excellent in non-stickiness is provided by the present invention.

In the water-in-oil emulsion composition according to the present invention, emulsification state is not deteriorated by stirring or shaking like in conventional Pickering emulsions, and temperature stability is also good since changes in physical properties of surfactants due to temperature is small like in emulsions obtained by conventional surfactants.

DESCRIPTION OF EMBODIMENTS

The water-in-oil emulsion composition is produced by using the oil-phase component (c) and the aqueous component (d), and the polyoxyalkylene/alkyl co-modified silicone and the core-corona particle (b) as emulsifiers.

(a) Polyoxyalkylene/Alkyl Co-Modified Silicone

In the present invention, a polyoxyalkylene/alkyl co-modified silicone type can be used as an emulsifier used together with the core-corona particle (b).

Examples of the polyoxyalkylene/alkyl co-modified silicones include: linear polyoxyalkylene/alkyl co-modified silicones such as cetyl PEG/PPG-10/1 dimethicone, or the like; and branched polyoxyalkylene/alkyl co-modified silicones such as lauryl PEG-9 polydimethylsiloxyethyl dimethicone, or the like. These surfactants can be used alone or in combination of a plurality of types. PEG is an abbreviation of polyethylene glycol, and PPG is an abbreviation of polypropylene glycol.

Among them, cetyl PEG/PPG-10/1 dimethicone and lauryl PEG-9 polydimethylsiloxyethyl dimethicone can be used preferably as the component (a) in the present invention. By using cetyl PEG/PPG-10/1 dimethicone and/or lauryl PEG-9 poly dimethylsiloxyethyl dimethicone together with the following component (b), a particularly stable water-in-oil emulsion composition can be obtained.

(b) Core-Corona Particle

The core-corona particle that can be used preferably in the present invention is a particle that has a core part consisting of a polymer having a relatively high hydrophobicity, and the corona part is stabilized by a polyethylene oxide chain that is a nonionic polymer. It is excellent in dispersion stability in water, acid resistance and salt resistance because of the polyethylene oxide chain of the corona part. The particle size is preferably almost uniform; and the average particle size may be within a range of 50 to 400 nm, and preferably 100 to 300 nm. Moreover, the degree of dispersion may be less than 0.2, and preferably less than 0.05.

The production methods of the core-corona particle are reported in Patent Literatures 2, 5, 6 and 7. It is disclosed that the core-corona particle is obtained by radically polymerizing a specific polyethylene oxide macromonomer and a specific hydrophobic monomer, under presence or absence of a specific crosslinking monomer, in a water-ethanol mixed solvent. Moreover, by dialyzing the obtained polymerization solution to water, the dispersion can be substituted to water.

The core-corona particle that can be used in the present invention can be obtained by radically polymerizing the monomers represented by the following formulae (1) to (4) under specific conditions.

<Polyethylene Oxide Macromonomer>

For example, commercially available products manufactured by Sigma-Aldrich Co. LLC, Blemmer® manufactured by NOF Corporation, or the like can be used as the polyethylene oxide macromonomer represented by the formula (1)

The molecular weight (i.e., value of n) of the polyethylene oxide part needs to be n=8 to 200.

Examples of such macromonomers include PME-400, PME-1000, and PME-4000 that are methoxy polyethylene glycol monomethacrylates (n values in the formula (1) are n=9, n=23, n=90, respectively; all manufactured by NOF corporation).

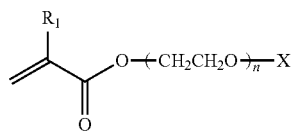

[Chem. 5]

(1) $R_1$ is a 1-3C alkyl group, and n is a number of 8 to 200. X is H or $CH_3$.

<Acrylate/Methacrylate Derivative Monomer>

For example, commercially available products manufactured by Sigma-Aldrich Co. LLC or Tokyo Chemical Industry Co., Ltd can be used as the acrylate/methacrylate derivative monomer represented by the formula (2).

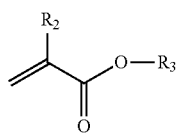

[Chem. (6)]

(2) $R_2$ is a 1-3C alkyl group.

$R_3$ is a 1-12C alkyl group, and more preferably a 1-8C alkyl group.

Examples of the acrylate/methacrylate derivative monomer include, but not limited to: methyl acrylate, ethyl acrylate, propyl acrylate, butyl acrylate, pentyl acrylate, hexyl acrylate, heptyl acrylate, octyl acrylate, decyl acrylate, dodecyl acrylate, methyl methacrylate, ethyl methacrylate, propyl methacrylate, butyl methacrylate, pentyl methacrylate, hexyl methacrylate, heptyl methacrylate, octyl methacrylate, decyl methacrylate, and dodecyl methacrylate. Methyl methacrylate, butyl methacrylate, and octyl methacrylate are particularly preferred.

These acrylate/methacrylate derivative monomers are generally-used raw materials, and can be easily obtained as general industrial raw materials.

<Acrylamide/Methacrylamide Derivative Monomer>

For example, t-butylacrylamide, N,N-dimethylacrylamide, N-[3-(dimethylamino)propyl]acrylamide, t-butylmethacrylamide, octylacrylamide, octylmethacrylamide, and octadecylacrylamide, or the like can be used preferably as the acrylamide/methacrylamide derivative monomer represented by the formula (3). Among these, t-butylacrylamide, N,N-dimethylacrylamide and N-[3-(dimethylamino)propyl] acrylamide are particularly preferred.

These acrylamide/methacrylamide monomers are available as commercial products or industrial raw materials.

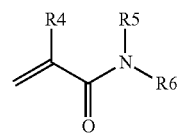

[Chem. 7]

(3) $R_4$ is H or a 1-3C alkyl group, and $R_5$ and $R_6$ are H or substituents having a 1-18C alkyl group.

<Crosslinking Monomer>

The crosslinking monomer represented by the formula (4) is available as commercial products or industrial raw materials. This crosslinking monomer is preferably hydrophobic.

The value of m is preferably 0 to 2. To be specific, ethylene glycol dimethacrylate (may be abbreviated as EGMA hereinbelow) manufactured by Sigma-Aldrich Co. LLC., Blemmer® PDE-50 manufactured by NOF Corporation, or the like are used preferably.

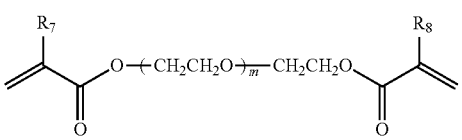

[Chem. 8]

(4) $R_7$ and $R_8$ are independently a 1-3C alkyl group, and m is a number of 0 to 2.

The core-corona particle dispersion that is a raw material for cosmetics according to the present invention may be one that is obtained by radically-polymerizing the above-identified monomers under the following conditions (A) to (E).

(A) A mole ratio expressed by a feed mole amount of the polyethylene oxide macromonomer/a feed mole amount of the hydrophobic monomer is 1:10 to 1:250.

(B) A feed amount of the crosslinking monomer relative to a feed amount of the hydrophobic monomer is 0.1 to 1.5% by mass.

(C) The hydrophobic monomer represented by the formula (2) has a monomer composition of which one type or two or more types of a methacrylic acid derivative having a 1-8C alkyl group is mixed.

(D) A polymerization solvent is a water-alcohol mixed solvent, and the alcohol is one type or two or more types selected from a group consisting of ethanol, dipropylene glycol, 1,3-butylene glycol and isoprene glycol.

(E) Solvent composition of the water-alcohol mixed solvent is water:alcohol=90 to 10:10 to 90 in a mass ratio at 20° C.

When the crosslinking monomer represented by the formula (4) is used in the present invention, "a feed amount of the crosslinking monomer relative to a feed amount of the hydrophobic monomer" is defined as a crosslink density (% by mass). In such case, with respect to the crosslink density of the core-corona particles used in the present invention, the feed amount of the crosslinking monomer relative to the feed amount of the hydrophobic monomer should be 0.1 to 1.5% by mass by Condition (B).

Next, each condition in cases when the crosslinking monomer represented by the formula (4) is used is described in detail.

(Condition (A))

The feed mole amounts of the polyethylene oxide macromonomer and the hydrophobic monomer can be polymerized when the feed mole amount of the polyethylene oxide macromonomer:the feed mole amount of the hydrophobic monomers is in the range of 1:10 to 1:250 (mole ratio). The feed mole amount is preferably in a range of 1:10 to 1:200, and more preferably in a range of 1:25 to 1:100.

When the mole amount of the hydrophobic monomer is less than 10 times of that of the polyethylene oxide macromonomer, the polymerized polymer becomes water soluble and does not form a core-corona polymer particle. In addition, when the mole amount of the hydrophobic monomer is 250 times or greater of that of the polyethylene oxide macromonomer, dispersion stabilization by the polyethylene oxide macromonomer becomes insufficient, so that the hydrophobic polymer by the insoluble hydrophobic monomer aggregates and precipitates.

(Condition (B))

A particle having the hydrophobic polymer of the core part crosslinked can be polymerized by co-polymerizing the crosslinking polymer.

When the feed amount of the crosslinking polymer is 0.10% by mass or less of that of the hydrophobic monomer, the crosslink density becomes low, and the particle may collapse upon swelling. When the feed amount exceeds 1.5% by mass, particles aggregate and preferred particles of narrow particle size distribution cannot be polymerized. The feed amount of the crosslinking monomer is preferably 0.2 to 1.0% by mass, more preferably 0.2 to 0.8% by mass, and most preferably 0.2 to 0.5% by mass.

(Condition (C))

The hydrophobic monomer represented by the formula (2) needs to have a monomer composition of which one type or two or more types of a methacrylate derivative having a 1-12C alkyl group is mixed. When the number of carbon atoms is zero (when it is a monomer without a terminal ester bond), the monomer may be too hydrophilic to be emulsion-polymerized adequately. Whereas, when the number of carbon atoms is 13 or greater, it may become steric hindrance upon polymerization, and a crosslink structure may not be constructed adequately.

(Condition (D))

The polymerization solvent needs to be a water-alcohol mixed solvent. An alcohol that can dissolve the hydrophobic monomer represented by formula (2) and the crosslinking monomer represented by the formula (3) is preferred. The alcohol used in the present invention needs to be ethanol, dipropylene glycol, 1,3-butylene glycol, or isoprene glycol.

When considering of being industrially manufacturable, that is using the polymerization solution without purification processes such as dialysis as a raw material as it is, the solvent to be mixed with water needs to be an alcohol that can be generally blended to cosmetics, not organic solvents that irritation upon application to skin is concerned such as ethanol, propanol, and butanol.

(Condition (E))

Solvent composition of the water-alcohol mixed solvent that is the polymerization solvent needs to be water:alcohol=90 to 10:10 to 90 in the mass ratio at 20° C. Solvent composition of the water-alcohol mixed solvent is preferably water:alcohol=90 to 10:10 to 90 (volume ratio at 20° C.), and more preferably water:alcohol=80 to 20:20 to 80 (volume ratio at 20° C.).

The polymerization solvent needs to be added with an alcohol in order to dissolve the hydrophobic monomer uniformly. The mixing ratio of the alcohol is 10 to 90 volume ratio. When the mixing ratio of the alcohol is less than 10 volume ratio, the dissolving ability of the hydrophobic monomer becomes extremely poor, polymerization proceeds in a monomer droplet state to form a gigantic lump, and thus the core-corona particle may not be formed. When the mixing ratio of the alcohol exceeds 90 volume ratio, an emulsion of the hydrophobic monomer by hydrophobic interaction may not be formed, emulsion-polymerization does not proceed, and thus the core-corona particle may not be obtained.

The polymerization solvent having a high monomer solubility is preferred. When production and purification processes (distillation, or the like) are considered, the viscosity and the boiling point are preferably not too high.

In the present invention, ethanol, dipropylene glycol, 1,3-butylene glycol, isoprene glycol or the like can be used preferably as the alcohol to be used as the polymerization solvent. Among the above, ethanol is particularly preferred.

Commercially available polymerization initiators used in common water-soluble thermal radical polymerization can be used as a polymerization initiator used in a polymerization system. When polymerization is performed without strictly controlling the stirring condition particularly in this polymerization system, an extremely narrow particle size distribution of the polymerized particle can be achieved.

When the crosslinking monomer represented by the formula (4) is not used, it may be polymerized under the condition described in Japanese Unexamined Patent Publication No. 2017-175011A, for example.

The core-corona particle (b) according to the present invention can be used together with the component (a) as an emulsifier for producing water-in-oil emulsion composition.

It was conventionally known that the core-corona particle emulsifies the oil-phase component and the aqueous-phase component to form the oil-in-water emulsion composition having a structure where the core-corona particle emulsifier is adsorbed onto the oil droplets of the oil-phase component dispersed in the aqueous-phase component (Patent Literature). In the present invention, it is considered that a change of some kind happens to the core-corona particle by coexistence of the polyoxyalkylene/alkyl co-modified silicone type surfactant (a); and it makes not the oil-phase component but the aqueous component into droplets to be extremely stably adsorbed onto the water droplets.

The blending amount of the core-corona particle (b) for producing the water-in-oil emulsion composition based on the pure content of the particle relative to the total amount of the composition is preferably 0.01 to 10% by mass, more preferably 0.03 to 5% by mass, and most preferably 0.05 to 1% by mass. When the blending amount is less than 0.01%, a stable cosmetic may be difficult to obtain. When the blending amount exceeds 10%, phase inversion to an oil-in-water emulsion may occur over time when the preparation is stored for a long term.

Moreover, the blending amount of the polyoxyalkylene/alkyl co-modified silicone (a) added for this purpose is preferably 0.5 to 3% by mass, more preferably 0.7 to 2% by mass, and most preferably 1% by mass. When the blending amount is less than 0.5% by mass, a stable water-in-oil emulsion may not be obtained. When the blending amount exceeds 3% by mass, feeling of use may deteriorate due to strong stickiness.

The water-in-oil emulsion composition of the present invention can be produced in accordance with common procedures. It may be produced by: mixing and dissolving an oil-phase component to which the polyoxyalkylene/alkyl co-modified silicone (a) is dissolved and other components; and adding thereto a dispersion obtained by mixing and dispersing the core-corona particle (b) to water or the aqueous-phase component, followed by emulsification by stirring and application of shear force.

(c) Oil-Phase Component

Examples of the oil-phase components include, but not limited to, hydrocarbon oils, higher fatty acids, higher alcohols, synthetic esters, silicone oils, liquid fats and oils, solid fats and oils, waxes, and perfumes that are commonly used in cosmetics, quasi-drugs, or the like.

Examples of hydrocarbon oils include, but not limited to, isododecane, isohexadecane, isoparaffin, liquid petrolatum, ozocerite, squalane, pristane, paraffin, ceresin, squalene, petrolatum, and microcrystallin wax.

Examples of higher fatty acids include, but not limited to, lauric acid, myristic acid, palmitic acid, stearic acid, behenic acid, oleic acid, undecylenic acid, tall oil, isostearic acid, linolic acid, linoleic acid, eicosapentaenoic acid (EPA), and docosahexaenoic acid (DHA).

Examples of higher alcohols include, but not limited to, straight chain alcohols (e.g., lauryl alcohol, cetyl alcohol, stearyl alcohol, behenyl alcohol, myristyl alcohol, oleyl alcohol, and cetostearyl alcohol), and branched chain alcohols (e.g., monostearyl glycerin ether (batyl alcohol)-2-decyltetradecynol, lanolin alcohol, cholesterol, phytosterol, hexyl dodecanol, isostearyl alcohol, and octyl dodecanol).

Examples of synthetic ester oils include, but not limited to, octyl octanoate, nonyl nonanoate, cetyl octanoate, isopropyl myristate, octyl dodecyl myristate, isopropyl palmitate, butyl stearate, hexyl laurate, myristyl myristate, decyl oleate, hexyl decyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylene glycol monoisostearate, neopentyl glycol dicaprate, tripropylene glycol pivalate, diisostearyl malate, glyceryl di-2-heptylundecanoate, glyceryl diisostearate, trimethylolpropane tri-2-ethyl hexanoate, trimethylolpropane triisostearate, pentaerythritol tetra-2-ethylhexanoate, glycerin tri-2-ethylhexanoate, glycerin trioctanoate, glycerin triisopalmitate, trimethylolpropane triisostearate, cetyl 2-ethyl hexanoate-2-ethylhexyl palmitate, glycerin trimyristate, tri-2-heptyl undecanoic acid glyceride, castor oil fatty acid methyl ester, oleyl oleate, aceto glyceride, 2-heptylundecyl palmitate, diisobutyl adipate, N-lauroyl-L-glutamic acid-2-octyldodecylester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oils include, but not limited to, chain polysiloxanes (e.g., dimethylpolysiloxane, methylphenyl polysiloxane, and diphenyl polysiloxane), ring polysiloxanes (e.g., octamethylcyclotetrasiloxane, decamethyl cyclopenta siloxane, and dodecamethyl cyclohexa siloxane), silicone resins forming a three-dimensional network structure, silicone rubbers, various modified polysiloxanes (amino-modified polysiloxanes, polyether-modified polysiloxanes, alkyl-modified polysiloxanes, and fluorine-modified polysiloxanes), and acryl silicones.

Examples of liquid fats and oils include, but not limited to, avocado oil, camellia oil, turtle oil, macadamia nut oil, corn oil, mink oil, olive oil, rapeseed oil, egg yolk oil, sesame oil, persic oil, wheat germ oil, sasanquan oil, castor oil, linseed oil, safflower oil, cotton seed oil, perilla oil, soybean oil, peanut oil, tea seed oil, Japanese nutmeg oil, rice bran oil, Chinese gimlet oil, Japanese gimlet oil, jojoba oil, germ oil, and triglycerin.

Examples of solid fats and oils include, but not limited to, cacao butter, coconut oil, horse fat, hydrogenated coconut oil, palm oil, beef tallow, mutton tallow, hydrogenated beef tallow, palm kernel oil, lard, beef bone fat, Japanese core wax nucleus oil, hydrogenated oil, neatsfoot oil, Japanese core wax, and hydrogenated castor oil.

Examples of waxes include, but not limited to, beeswax, candelilla wax, cotton wax, camauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

Selection of the perfume is not limited in particular; examples include natural perfumes from animals or plants, synthetic perfumes prepared by means of chemical synthesis, and perfume blends thereof. By blending perfume, a cosmetic having a superior durability of fragrance can be obtained.

Specific examples of perfumes include, but not limited to, acetivenol, anise aldehyde, anethole, amyl acetate, amyl salicylate, allyl amyl glycolate, allyl caproate, aldehyde C6-20, ambrettolide, ambrettolide, ambroxan, ionone, Iso E Super, eugenol, auranthiol, galaxolide, calone, coumarin, geraniol, geranyl acetate, Sandalore, santalol, sandela, cyclamen aldehyde, cis-3-hexenyl acetate, cis-3-hexenol, citral, citronellyl acetate, citronellol, cineole, dihydromyrcenol, jasmolactone, cinnamic alcohol, cinnamic aldehyde, styralyll acetate, cedryl acetate, cedrol, damascone, damascenone, decalactone, terpinyl acetate, terpineol, tonalid, tonalide, triplal, nerol, bacdanol, vanillin, hydroxycitronellal, phenylethyl acetate, phenylethyl alcohol, hexyl salicylate, vetiveryl acetate, hedione, heliotropin, helional, vertofix, benzyl acetate, benzyl salicylate, benzyl benzoate, pentalide, pentalide, bornyl acetate, myol, musk ketone, methyl anthranilate, methyl dihydrojasmonate, yara yara, lime oxide, linalyl acetate, linalool, limonene, Lyral, lilial, rose oxide, rhodinol, Angelica oil, anise oil, Artemisia vulgaris oil, basil oil, bay oil, Bergamot oil, calamus oil, camphor oil, cananga oil, cardamom oil, cassia oil, cedar wood oil, celery oil, chamomile oil, cinnamon oil, clove oil, coriander oil, cumin oil, dill oil, elemi oil, estragon oil, eucalyptus oil, fennel oil, fenugreek oil, galbanum oil, geranium oil, ginger oil, grapefruit oil, gaiac wood oil, cypress leaf oil, cypress oil, juniper berry oil, lavandin oil, lavender oil, lemon oil, lime oil, mandarin oil, ziram oil, mimosa oil, peppermint oil, spearmint oil, mill oil, myrtle oil, nutmeg oil, oakmoss oil, olibanum oil, opoponax oil, orange oil, parsley oil, patchouli oil, pepper oil, perilla oil, petit grain oil, neroli oil, orange flower oil, pimento oil, all spice oil, pine oil, rose oil, rosemary oil, clary sage oil, sage oil, sandalwood oil, styrax oil, taget oil, thyme oil, tuberose oil, valerian oil, vetiver oil, violet leaf oil, wintergreen oil, wormwood oil, ylang ylang oil, yuzu oil, cassie absolute, genet absolute, hyacinth absolute, immortelle absolute, jasmine absolute, jonquil absolute, narcis absolute, rose absolute, violet leaf absolute, and benzoin.

In emulsion compositions obtained by conventional surfactants, the physical properties of surfactants and the physical properties of oil components greatly affect emulsifiability, and measures such as changing the types of surfactants needed to be taken when changing the oil-phase component. However, since the water-in-oil emulsion composition of the present invention is emulsified by the core-corona particle (b), emulsifiability and stability are less affected by the types of oil components, and the oil component in a wider range than before can be blended.

(c) Aqueous Component

Water, water soluble alcohols, thickeners, or the like commonly used in cosmetics, quasi-drugs, or the like can be blended as the aqueous-phase component; in addition, appropriate amounts of moisturizers, chelating agents, preservatives, pigments, or the like can also be blended as desired.

Water contained in the oil-in-water emulsion composition of the present invention is not limited in particular; and examples thereof include, but not limited to, purified water, ion-exchanged water, and tap water.

Examples of water-soluble alcohols include lower alcohols, polyhydric alcohols, polyhydric alcohol polymers, dihydric alcohol alkyl ethers, dihydric alcohol ether esters, glycerin monoalkyl ethers, sugar alcohols, monosaccharides, oligosaccharides, polysaccharides, and derivatives thereof.

Examples of lower alcohols include, but not limited to, ethanol, propanol, isopropanol, isobutyl alcohol, and t-butyl alcohol.

Examples of polyhydric alcohols include, but not limited to: dihydric alcohols (e.g., dipropylene glycol, 1,3-butylene glycol, ethylene glycol, trimethylene glycol, 1,2-butylene glycol, tetramethylene glycol, 2,3-butylene glycol, pentamethylene glycol, 2-butene-1,4-diol, hexylene glycol, and octylene glycol); trihydric alcohols (e.g., glycerin and trimethylolpropane); tetrahydric alcohols (e.g., diglycerin, pentaerythritols such as 1,2,6-hexanetriol); pentahydric alcohols (e.g., xylitol and triglycerin); hexahydric alcohols (e.g., sorbitol, and mannitol); polyhydric alcohol polymers (e.g., diethylene glycol, dipropylene glycol, triethylene glycol, polypropylene glycol, tetraethylene glycol, diglycerin, triglycerin, tetraglycerin, and polyglycerin); dihydric alcohol alkyl ethers (e.g., ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (e.g., diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin mono alkyl ethers (e.g., xylyl alcohol, selachyl alcohol, and batyl alcohol); sugar alcohols (e.g., maltotriose, mannitol, sucrose, erythritol, glucose, fructose, starch amylolysis sugar, maltose, and alcohols prepared by the reduction of starch amylolysis sugar); glysolid; tetrahydro furfuryl alcohol; POE-tetrahydro furfuryl alcohol; POP-butyl ether; POP/POE-butyl ether tripolyoxypropylene glycerin ether; POP-glycerin ether; POP-glycerin ether phosphoric acid; POP/POE-pentane erythritol ether; and polyglycerin.

Examples of monosaccharides include, but not limited to: trioses (e.g., D-glyceryl aldehyde, and dihydroxyacetone); tetroses (e.g., D-etythrose, D-erythrulose, D-threose, and erythritol); pentoses (e.g., L-arabinose, D-xylose, L-lyxose, D-arabinose, D-ribose, D-ribulose, D-xylulose, and L-xylulose); hexoses (e.g., D-glucose, D-talose, D-psicose, D-galactose, D-fructose, L-galactose, L-mannose, and D-tagatose); heptoses (e.g., aldoheptose and heprose); octoses (e.g., octurose); deoxysugars (e.g., 2-deoxy-D-ribose, 6-deoxy-L-galactose, and 6-deoxy-L-mannose); amino sugars (e.g., D-glucosamine, D-galactosamine, sialic acid, amino uronic acid, and muramic acid); and uronic acid (e.g., D-glucuronic acid, D-mannuronic acid, L-guluronic acid, D-galacturonic acid, and L-iduronic acid).

Examples of oligosaccharides include, but not limited to, sucrose, gentianose, umbelliferose, lactose, planteose, isolignoses, α, α-trehalose, raffinose, lignoses, umbilicine, stachyose, and verbascoses.

Examples of polysaccharides include, but not limited to, cellulose, quince seed, starch, galactan, dermatan sulfate, glycogen, gum arabic, heparan sulfate, traganth gum, keratan sulfate, chondroitin, xanthan gum, guar gum, dextran, kerato sulfate, locust bean gum, and succinoglucan.

Examples of other polyols include, but not limited to, polyoxyethylene methyl glucoside (Glucam E-10), and polyoxypropylene methyl glucoside (Glucam P-10).

Examples of thickeners include, but not limited to: gum arabic, carrageenan, karaya gum, gum tragacanth, carob gum, quince seed (*Cydonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (Veegum), laponite, and silicic acid anhydride.

Examples of natural water-soluble polymers include, but not limited to: plant-type polymers (e.g., gum arabic, gum tragacanth, galactan, guar gum, carob gum, karaya gum, carrageenan, pectin, agar, quince seed (*Cydonia oblonga*), algae colloids (brown algae extract), starches (rice, corn, potato, wheat), and glycyrrhizic acid); microorganism-type polymers (e.g., xanthan gum, dextran, succinoglucan, and pullulan); and animal-type polymers (e.g., collagen, casein, albumin, and gelatin).

Examples of semisynthetic water-soluble polymers include, but not limited to: starch-type polymers (e.g., carboxymethyl starch and methylhydroxypropyl starch); cellulosic polymers (e.g., methyl cellulose, ethyl cellulose, methylhydroxypropyl cellulose, hydroxyethyl cellulose, cellulose sodium sulfate, hydroxypropyl cellulose, carboxymetyl-cellulose, sodium carboxymethyl cellulose, crystal cellulose, and cellulose powder); and alginic acid-type polymers (e.g., sodium alginate and propylene glycol alginate).

Examples of synthetic water-soluble polymers include, but not limited to: vinyl-type polymers (e.g., polyvinyl alcohol, polyvinyl methyl ether, polyvinylpyrrolidone, and carboxy vinyl polymer); polyoxyethylene-type polymers (e.g., polyethylene glycol 20,000, 40,000, 60,000); acrylic polymers (e.g., sodium polyacrylate, polyethylacrylate, and polyacrylamide); polyethyleneimine; and cationic polymers.

Examples of moisturizers include, but not limited to, chondroitin sulfate, hyaluronic acid, mucoitin sulfuric acid, charonic acid, atelocollagen, cholesteryl-12-hydroxy stearate, sodium lactate, bile salt, DL-pyrrolidone carboxylic acid salt, short chain soluble collagen, diglycerin (EO)PO adduct, chestnut rose fruit extract, yarrow extract, and sweet clover extract.

Examples of sequestrants include, but not limited to, 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediaminehydroxyethyl triacetate.

Examples of amino acids include, but not limited to, neutral amino acids (e.g., threonine and cysteine), and basic amino acids (e.g., hydroxylysine). Examples of amino acid derivatives include, but not limited to, sodium acyl sarcosinate (sodium N-lauroyl sarcosinate), acyl glutamate, sodium acyl β-alanine, and glutathione.

Examples of pH adjusters include, but not limited to, buffers such as lactic acid-sodium lactate, citric acid-sodium citrate, and succinic acid-sodium succinate.

The blending amounts of the oil-phase components and the aqueous-phase components blended to the water-in-oil emulsion composition of the present invention are not particularly limited. By using the polyoxyalkylene/alkyl co-modified silicone (a) and the core-corona particle (b) together as the emulsifier, a water-in-oil emulsion composition having a wide range of the oil-phase component/aqueous-phase component ratio can be obtained; the water-in-oil emulsion composition ranging from embodiments having a small oil-phase component/aqueous-phase component ratio, i.e., the oil-phase component is blended at a small amount (emulsions, or the like), to embodiments of which the oil-phase component is blended at a large amount (cleansing creams, sunscreens, hair creams, etc.), can be obtained.

Other components commonly used in cosmetics and quasi-drugs can be blended as necessary in the water-in-oil emulsion composition according to the present invention as long as the effect of the present invention is not adversely affected; examples of such components include, but not limited to, ultraviolet absorbents, powders, organic amines, polymer emulsions, vitamins, and antioxidants.

Examples of water-soluble ultraviolet absorbents include, but not limited to: benzophenone-type ultraviolet absorbents such as 2,4-dihydroxybenzophenone, 2,2'-dihydroxy-4-methoxy benzophenone, 2,2'-dihydroxy-4,4'-dimethoxybenzophenone, 2,2',4,4'-tetrahydroxy benzophenone, 2-hydroxy-4-methoxy benzophenone, 2-hydroxy-4-methoxy-4'-methylbenzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxy benzophenone, 4-hydroxy-3-carboxy benzophenone; benzimidazole-type ultraviolet absorbents such as phenylbenzimidazole-5-sulfonic acid and salts thereof and phenylene-bis-benzimidazole-tetrasulfonic acid and salts thereof; 3-(4'-methylbenzylidene)-d,l-camphor; 3-benzylidene-d,l-camphor; urocanic acid; and urocanic acid ethyl ester.

Examples of oil-soluble ultraviolet absorbents include, but not limited to: benzoic acid-type ultraviolet light absorbents such as para-aminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester; anthranilic acid-type ultraviolet light absorbents such as homo mentyl-N-acetyl anthranilate; salicylic acid-type ultraviolet light absorbents such as amyl salicylate, mentyl salicylate, homo mentyl salicylate, octyl salicylate, phenyl salicylate, benzyl salicylate, p-isopropanol phenyl salicylate; cinnamic acid-type ultraviolet absorbents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate, 2-ethylhexyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethyl hexanoyl-diparamethoxy cinnamate, 3-methyl-4-[methylbis(trimethylsiloxy)silyl]butyl 3,4,5-trimethoxy cinnamate; 2-phenyl-5-methyl benzoxazole, 2,2'-hydroxy-5-methylphenyl benzotriazol, 2-(2'-hydroxy-5'-t-octylphenyl) benzotriazol, 2-(2'-hydroxy-5'-methylphenyl)benzotriazol, dibenzaladine, dianisoylmethane, 4-methoxy-4'-t-butyl dibenzoyl-methane, and 5-(3,3-dimethyl-2-norbornylidene)-3-pentane-2-one, and octocrylene.

Examples of powder components include, but not limited to, inorganic powders (e.g., talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, calcined calcium sulfate (calcined gypsum), calcium phosphate, fluorine-apatite, hydroxy apatite, ceramic powder, metallic soaps (e.g., zinc myristate, calcium palmitate, aluminum stearate), and boron nitride); organic powders (e.g., polyamide resin powder (nylon powder), polyethylene powder, poly-methyl methacrylate powder, polystyrene powder, powders of the copolymer resin of styrene and acrylic acid, benzoguanamine resin powder, polytetrafluoroethylene powder, and cellulose powder); inorganic white pigments (e.g., titanium dioxide and zinc oxide); inorganic red pigments (e.g., iron oxide (red iron oxide) and iron titanate); inorganic brown pigments (e.g., .gamma.-iron oxide); inorganic yellow pigments (e.g., yellow iron oxide and loess); inorganic black pigments (e.g., black iron oxide and low oxides of titanium.); inorganic purple pigments (e.g., mango violet and cobalt violet); inorganic green pigments (e.g., chromium oxide, chromium hydroxide, and cobalt titanate); inorganic blue pigments (e.g., ultramarine blue and Berlin blue); pearl pigments (e.g., titanium oxide coated mica, titanium oxide coated bismuth oxychloride, titanium oxide coated talc, coloration titanium oxide coated mica, bismuth oxychloride, and fish scale flakes); metal powder pigments (e.g., aluminum powder and copper powder); organic pigments such as zirconium, barium or aluminum rake (e.g., organic pigments such as red 201, red 202, red 204, red 205, red 220, red 226, red 228, red 405, orange 203, orange 204, yellow 205, yellow 401, and blue 404, as well as red 3, red 104, red 106, red 227, red 230, red 401, red 505, orange 205, yellow 4, yellow 5, yellow 202, yellow 203, green 3 and blue 1); and natural colors (e.g., chlorophyll and (3-carotene).

Examples of organic amines include, but not limited to, monoethanolamine, diethanolamine, triethanolamine, morpholine, tetrakis(2-hydroxypropyl)ethylenediamine, triisopropanolamine, 2-amino-2-methyl-1,3-propanediol, and 2-amino-2-methyl-1-propanol.

Examples of polymer emulsions include, but not limited to, acrylic resin emulsions, ethyl polyacrylate emulsions, acryl resin liquids, polyacrylic alkyl ester emulsions, polyvinyl acetate resin emulsions, and natural rubber latex.

Examples of vitamins include, but not limited to, vitamins A, B1, B2, B6, C and E as well as their derivatives, pantothenic acid and its derivatives, and biotin.

Examples of antioxidants include, but not limited to, tocopherols, dibutyl hydroxytoluene, butyl hydroxyanisole, and gallic acid esters.

Examples of antioxidant aids include, but not limited to, phosphoric acid, citric acid, ascorbic acid, maleic acid, malonic acid, succinic acid, fumaric acid, cephalin, hexametaphosphate, phytic acid, and ethylene diamine tetraacetic acid.

Examples of other components that can be belended include, but not limited to, antiseptics (methylparaben, ethylparaben, butylparaben, and phenoxyethanol); antiphlogistic agents (e.g., glycyrrhizic acid derivatives, glycyrrhetinic acid derivatives, salicylic acid derivatives, hinokitiol, zinc oxide, and allantoin); whitening agents (e.g., placenta extract, creeping saxifrage extract, and arbutin); various extracts (e.g., Phellodendri Cortex, goldthread, lithospermum root, Paeonia lactiflora, Swertia japonica, birch, sage, loquat, carrot, aloe, Malva sylvestris, iris, grape, Coix mayuen, sponge gourd, lily, saffron, Cnidium officinale, sheng jiang, Hypericum erectum, Ononis, garlic, Guinea pepper, chen pi, Ligusticum acutilobum, and seaweed), activators (e.g., royal jelly, photosensitive substances, and cholesterol derivatives); blood circulation promoters (e.g., nonyl acid valenyl amide, nicotinic acid benzyl esters, nicotinic acid β-butoxy ethyl esters, capsaicin, gingeron, cantharis tincture, Ichthammol, tannic acid, α-bomeol, tocopherol nicotinate, inositol hexanicotinate, cyclandelate, cinnarizine, tolazoline, acetylcholine, verapamil, cepharanthine, and γ-orizanol); anti-seborrhea agents (e.g., sulfur, and thiantol); and anti-inflammatory agents (e.g., tranexamic acid, thiotaurine, and hypotaurine).

Moreover, not as the emulsifier, but for the purpose of controlling tactile sensations during use, controlling drug permeation and such, or improving washing ability when blended into washing agents for skin or hair, other surfactants can be blended as the aqueous-phase or oil-phase component to the water-in-oil emulsion composition of the present invention.

An ampholytic surfactant has at least one cationic functional group and one anionic functional group, is cationic when the solution is acidic and anionic when the solution is alkaline, and has characteristics similar to a nonionic surfactant around the isoelectric point.

Ampholytic surfactants are classified, based on the type of the anionic group, into the carboxylic acid type, the sulfuric ester type, the sulfonic acid type, and the phosphoric ester type. The carboxylic acid type, the sulfuric ester type, and the sulfonic acid type are preferred in the present invention. The carboxylic acid type is further classified into the amino acid type and the betaine type. The betaine type is particularly preferred.

Specific examples include, but not limited to: imidazoline type ampholytic surfactants (e.g., 2-undecyl-N,N,N-(hydroxyethyl carboxymethyl)-2-imidazoline sodium salt and 2-cocoyl-2-imidazolinium hydroxide-1-carboxyethyloxy 2 sodium salt); and betaine type surfactants (e.g., 2-heptadecyl-N-carboxymethyl-N-hydroxyethyl imidazolinium betaine, lauryldimethylaminoacetic acid betaine, alkyl betaine, amide betaine, and sulfobetaine).

Examples of cationic surfactants include, but not limited to, quaternary ammonium salts such as cetyltrimethylammonium chloride, stearyltrimethylammonium chloride, behenyltrimehylammonium chloride, behenyldimethylhydroxyethylammonium chloride, stearyldimethylbenzylammonium chloride, and cetyltrimethylammonium methyl sulfate. Other examples include, but not limited to, amide amine compounds such as stearic diethylaminoethylamide, stearic dimethylaminoethylamide, palmitic diethylaminoethylamide, palmitic dimethylaminoethylamide, myristic diethylaminoethylamide, myristic dimethylaminoethylamide, behenic diethylaminoethylamide, behenic dimethylaminoethylamide, stearic diethylaminopropylamide, stearic dimethylaminopropylamide, palmitic diethylaminopropylamide, palmitic dimethylaminopropylamide, myristic diethylaminopropylamide, myristic dimethylaminopropylamide, behenic diethylaminopropylamide, and behenic dimethylaminopropylamide.

Anionic surfactants are classified into the carboxylate type such as fatty acid soaps, N-acyl glutamates, and alkyl ether acetates, the sulfonic acid type such as α-olefin sulfonates, alkane sulfonates, and alkylbenzene sulfonates, the sulfuric ester type such as higher alcohol sulfuric ester salts, and the phosphoric ester salt type. The carboxylate type, the sulfonic acid type, and the sulfuric ester salt type are preferred; and the sulfuric ester salt type is particularly preferred.

Specific examples include, but not limited to, fatty acid soaps (e.g., sodium laurate and sodium palmitate); higher alkyl sulfuric acid ester salts (e.g., sodium lauryl sulfate and potassium lauryl sulfate); alkyl ether sulfuric acid ester salts (e.g., POE-triethanolamine lauryl sulfate and sodium POE-lauryl sulfate); N-acyl sarcosinic acids (e.g., sodium lauroyl sarcosinate); higher fatty acid amide sulfonic acid salts (e.g., sodium N-myristoyl N-methyl taurate, sodium cocoyl methyl taurate, and sodium laurylmethyl taurate); phosphoric ester salts (e.g., sodium POE-oleyl ether phosphate and POE-stearyl ether phosphoric acid); sulfosuccinates (e.g., sodium di-2-ethylhexylsulfosuccinate, sodium monolauroyl monoethanol amide polyoxyethylene sulfosuccinate, and sodium lauryl polypropylene glycol sulfosuccinate); alkyl benzene sulfonates (e.g., sodium linear dodecyl benzene sulfonate, triethanolamine linear dodecyl benzene sulfonate, and linear dodecyl benzene sulfonic acid); higher fatty acid ester sulfates (e.g., hydrogenated coconut oil aliphatic acid glycerin sodium sulfate); N-acyl glutamates (e.g., mono sodium N-lauroylglutamate, disodium N-stearoylglutamate, and mono sodium N-myristoyl-L-glutamate); sulfated oils (e.g., turkey red oil); POE-alkyl ether carboxylic acid; POE-alkyl aryl ether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

A nonionic surfactant is a surfactant that is not ionized to bear an electric charge in an aqueous solution. Specific examples include, but not limited to, glycerol fatty acid esters, ethylene oxide derivatives of glycerol fatty acid esters, polyglycerol fatty acid esters, propylene glycol fatty acid esters, ethylene oxide derivatives of propylene glycol fatty acid esters, polyethylene glycol fatty acid esters, polyethylene glycol alkyl ethers, polyethylene glycol alkyl phenyl ethers, polyethylene glycol castor oil derivatives, and polyethylene glycol hydrogenated castor oil derivatives.

Examples of hydrophilic nonionic surfactants include, but not limited to, POE-sorbitan fatty acid esters (e.g., POE-sorbitan monooleate, POE-sorbitan monostearate, POE-sorbitan monooleate, and POE-sorbitan tetraoleate); POE sorbitol fatty acid esters (e.g., POE sorbitol monolaurate, POE-sorbitol monooleate, POE-sorbitolpentaoleate, and POE-sorbitol monostearate); POE-glycerin fatty acid esters (e.g., POE-monooleates such as POE-glycerin monostearate, POE-glycerin monoisostearate, and POE-glycerin triisostearate); POE-fatty acid esters (e.g., POE-distearate, POE-monodioleate, and ethylene glycol distearate); POE-alkylethers (e.g., POE-lauryl ether, POE-oleyl ether, POE-stearyl ether, POE-behenyl ether, POE-2-octyl dodecyl ether, and POE-cholestanol ether); pluaronics (e.g., pluaronic); POE-POP-alkylethers (e.g., POE-POP-cetyl ether, POE-POP-2-decyl tetradecyl ether, POE-POP-monobutyl ether, POE-POP-lanolin hydrate, and POE-POP-glycerin ether); tetra POE-tetra POP-ethylenediamino condensates (e.g., tetronic); POE-castor oil hydrogenated castor oil derivatives (e.g., POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax-lanolin derivatives (e.g., POE-sorbitol beeswax); alkanol amides (e.g., palm oil fatty acid diethanol amide, laurate monoethanolamide, and fatty acid isopropanol amide); POE-propylene glycol fatty acid esters; POE-alkylamines; POE-fatty acid amides; sucrose fatty acid esters; alkyl ethoxydimethylamine oxides; and trioleyl phosphoric acid.

Applications of the water-in-oil emulsion composition of the present invention are not limited in particular; however, it is preferred as skin cosmetics, hair cosmetics, skin external preparations, or the like.

EXAMPLES

The present invention will be described with reference to the following examples, but the present invention is not limited thereto. The blending amounts are expressed with "% by mass" unless otherwise specified. The blending amounts of the core-corona particles in Tables 3 to 5 are the converted values of the pure content of the particles.

Test Example 1: Production of a Core-Corona Particle

<Production Method>

Production Example 1

A polyethyleneoxide macro monomer, a hydrophobic monomer, and a crosslinking monomer were added to a water-alcohol mixed solvent in a three-neck flask equipped with a reflux tube and a nitrogen feeding tube. After sufficient dissolution or dispersion, 1 mol % of the polymerization initiator, 2,2'-azobis(2-methylpropionamidine) dihydrochloride, relative to the total amount of the monomers, was dissolved in a small amount of water and added, and further dissolution or dispersion was carried out. The uniformly dissolved or dispersed polymerization solution was put through nitrogen substitution for 20 minutes to remove dissolved oxygen, followed by 8 hours of polymerization with stirring by means of a magnetic stirrer while the temperature was maintained at 65 to 70° C. in an oil bath. After the completion of polymerization, the polymer solution was returned to room temperature to obtain a core-corona particle dispersion (production example 1).

In the production of the core-corona particle dispersion, Blemmer PME-4000 (manufactured by NOF CORPORATION; $n \approx 9$ in the macromonomer represented by Formula (1)) was used as the polyethylene oxide macro-monomer. Methyl methacrylate (MMA) and butyl methacrylate (n-BMA) were used as the hydrophobic monomer. Ethylene glycol dimethacrylate (EGDMA) was used as the crosslinking monomer.

Production Example 2

A polyethyleneoxide macro monomer and a hydrophobic monomer were added to a water-alcohol mixed solvent in a three-neck flask equipped with a reflux tube and a nitrogen feeding tube. After sufficient dissolution or dispersion, dissolved oxygen was removed by nitrogen substitution for 20 minutes. Then, 1 mol % of the polymerization initiator, 2,2'-azobis(2-methylpropionamidine) dihydrochloride, relative to the total amount of the monomers, was dissolved in a small amount of water and added, and further dissolution or dispersion was carried out. The uniformly dissolved or dispersed polymerization solution was put through nitrogen substitution for 20 minutes to remove dissolved oxygen, followed by 8 hours of polymerization with stirring by means of a magnetic stirrer while the temperature was maintained at 65 to 70° C. in an oil bath. After the completion of polymerization, the polymer solution was returned to room temperature to obtain a core-corona particle dispersion.

In the above, Blemmer PME-4000 (manufactured by NOF CORPORATION) was used as the polyethylene oxide macro-monomer. Methyl methacrylate (MMA), butyl methacrylate (n-BMA), t-butylacrylamide (t-BAA), and N-[3-(dimethylamino)propyl]acrylamide (DMAPA) were used as the hydrophobic monomer.

<Method for Measuring the Particle Size and the Degree of Dispersion>

The particle size of the core-corona particle (hereinafter may be referred simply as "particle") was measured with a Zetasizer manufactured by Malvern Instruments Ltd. A measurement sample of the core-corona particle dispersion having the particle concentration of about 0.1% was prepared by dilution with water. After removing dust with a 0.45 μm filter, the scattering intensity at 25° C. was measured at the scattering angle of 173° (back-scattered light), and the average particle size and the degree of dispersion were calculated with analysis software installed on the measurement apparatus. The particle size was analyzed by the cumulant analysis method, and the degree of dispersion is a normalized value of the second-order cumulant value obtained by the cumulant analysis. This degree of dispersion is a commonly used parameter, and can be automatically analyzed with a commercial dynamic light scattering measurement apparatus. For the viscosity of the solvent, which is necessary for the particle size analysis, the viscosity of pure water at 25° C., i.e., 0.89 mPa s, was used.

The polymerization conditions used in Production examples 1 and 2 are shown in Tables 1 to 3 below. The numerical values in Table 1 are all in g (grams). Moreover, EtOH in the tables is an abbreviation of ethanol.

TABLE 1

|  | Macromonomer BLEMMER | Hydrophobic monomer | | | | Crosslinking monomer | Polymerization solvent | |
| --- | --- | --- | --- | --- | --- | --- | --- | --- |
|  | PME-4000 Formula (1) | MMA Formula (2) | n-BMA | t-BAA Formula (3) | DMAPA | EGDMA Formula (4) | Water | Alcohol (EtOH) |
| Production example 1 | 4.04 | 2.45 | 3.47 |  |  | 0.03 | 54 | 36 |
| Production example 2 | 4.06 | 2.4 | 3.41 | 0.06 | 0.08 |  | 54 | 36 |

TABLE 2

| | (A)Macromonomer/ hydrophobic monomer ratio (mole ratio) | (B) Feed mount of crosslinking monomer (% by mass) | (E) Water/alcohol mixing ratio (mass ratio) |
|---|---|---|---|
| Production example 1 | 1/50 | 0.5 | 60/40 |
| Production example 2 | 1/50 | — | 60/40 |

TABLE 3

| | BLEMMER PME-4000 Formula (1) | MMA Formula (2) | n-BMA | t-BAA | DMAPA Formula (3) | EGDMA Formula (4) |
|---|---|---|---|---|---|---|
| Production example 1 | $R_1 = CH_3$<br>n = 90 | $R_2 = CH_3$<br>$R_3 = CH_3$ | $R_2 = CH_3$<br>$R_3 = nC_4H_9$ | — | — | $R_7 = CH_3$<br>$R_8 = CH_3$<br>m = 1 |
| Production example 2 | | | | $R_4 = H$<br>$R_5 = H$<br>$R_6 = tC_4H_9$ | $R_4 = H$<br>$R_5 = H$<br>$R_6 = C_2H_4N(CH_3)_2$ | — |

The particle sizes and the degrees of dispersion were 206.1 nm and 0.052 in Production example 1, and 210.3 nm and 0.018 in Production example 2, respectively.

Test Example 2: Production of an Emulsion Composition

Emulsion compositions were prepared with the core-corona particle produced in Test Example 1, and (1) a phase state, and (2) emulsification stability were analyzed in accordance with the following methods. The formulations and results are shown in Table 4.

<Production Method 1>
An oil-phase component (c) and a polyoxyalkylene/alkyl co-modified silicone (a) were mixed. In addition, the core-corona particle dispersion (b) produced in Test example 1 was added to an aqueous-phase component (d), and mixed with stirring to uniformly disperse the core-corona particles in the aqueous-phase component. The mixed solution consisting of the components (c) and (a) was added to an aqueous dispersion consisting of the components (b) and (d), and was subjected to shear mixing with a homomixer until homogeneous.

<Production Method 2>
An oil-phase component (c) and a polyoxyalkylene/alkyl co-modified silicone (a) were mixed. In addition, the core-corona particle dispersion (b) produced in Test example 1 was added to an aqueous-phase component (d) and mixed with stirring to uniformly disperse the core-corona particles in the aqueous-phase component. This aqueous dispersion was added to the mixed solution consisting of the components (c) and (a), and was subjected to shear mixing with a homomixer until homogeneous.

Evaluation (1) Phase State
A phase state of the sample was observed with an optical microscope.

(2-1) Emulsification Stability
After subjecting the sample to a centrifugal treatment with a centrifugal separator (3500 rpm, 120 minutes), the emulsification state was observed with an optical microscope. It was evaluated in accordance with the following criteria. Stability of the emulsion particles to stirring or shaking can be evaluated by this analysis. A or greater was regarded as acceptable in the present invention.

A: The emulsion particles were homogeneous, and no coalescence or aggregation was observed.
B: The emulsion particles were mostly homogeneous, but slight coalescence or aggregation was observed.
C: The emulsion particles were not homogeneous, and significant coalescence or aggregation was observed.

TABLE 4

| | | | Comparative example 1 | Comparative example 2 | Example 1 |
|---|---|---|---|---|---|
| | Production method | | Production method 1 | Production method 2 | Production method 1 |
| Formulation | (c) | Cyclopentasiloxane | 50 | 50 | 50 |
| | | Core-corona particle (Production example 1) | 1 | 1 | 1 |
| | (a) | Lauryl PEG-9 polydimethylsiloxyethyl dimethicone | | | 1 |
| | (d) | Ethanol | 3.6 | 3.6 | 3.6 |
| | | Ion-exchanged water | Balance | Balance | Balance |
| | | Total | 100 | 100 | 100 |

TABLE 4-continued

|  |  | Comparative example 1 | Comparative example 2 | Example 1 |
|---|---|---|---|---|
| Evaluation | (1) Phase state | O/W | Insufficient emulsification | W/O |
|  | (2-1) Emulsification stability | A | — | A |

As described above, the core-corona particle is widely known as an emulsifier for producing an oil-in-water emulsion composition (Patent Literature 1, or the like). As shown in Table 4, the composition (Comparative example 1) of which the oil component was emulsified with the core-corona particle in accordance with the general production method for the oil-in-water emulsion composition (Production method 1) became an oil-in-water emulsion composition having a high emulsification stability.

Whereas, the composition (Example 1) of which lauryl PEG-9 poly dimethylsiloxyethyl dimethicone, which is the polyoxyalkylene/alkyl co-modified silicone, was added to the formulation of Comparative example 1 surprisingly became a water-in-oil emulsion composition, even if it was produced in accordance with the production method for the oil-in-water emulsion composition (Production method 1). Moreover, this water-in-oil emulsion composition was excellent in emulsification stability.

When production of an emulsion was tried in accordance with the general production method for the water-in-oil emulsion composition (Production method 2) with the formulation of Comparative example 1, emulsification was insufficient, and thus an emulsion could not be obtained.

Accordingly, it was shown that the core-corona particle that is known to produce an oil-in-water emulsion system produced a stable water-in-oil emulsion system under coexistence with a specific surfactant.

Test Example 3: Investigation on Components

The surfactant that produces a water-in-oil emulsion when used together with the core-corona particle was investigated. The emulsion compositions were produced by the same method as Test example 2, and, in addition to the above-identified items, the following items were evaluated in accordance with the following criteria. The results are shown in Tables 5 and 6.

Evaluation (3) Emulsion Particle Size
The emulsion particle size of the sample was measured with an optical microscope.

(2-1) Emulsification Stability (Centrifugal Treatment)
The sample was put into a test tube to be subjected to centrifuge treatment at 3500 rpm for two hours. Then, the state of the sample was visually observed in accordance with the following criteria. Dynamic stability (coalescence stability) of the emulsion system can be evaluated by this analysis. A or greater was regarded as acceptable in the present invention.
  A: The sample maintained the emulsification state at the time of production.
  B: Due to coalescence of some emulsion particles, the aqueous phase was slightly separated.
  C: All emulsion particles coalesced, and the aqueous phase was completely separated.

(2-2) Emulsification Stability
After storing the sample at 50° C. for four weeks, the state of the sample was visually observed in accordance with the following criteria. Temperature stability and stability overtime of the emulsion system can be evaluated by this analysis. When providing this composition in commercial base, this index is more important than (2-1). A or greater was regarded as acceptable in the present invention.
  A: The sample maintained the emulsification state at the time of production.
  B: Due to coalescence of some emulsion particles, the aqueous phase was slightly separated.
  C: All emulsion particles coalesced, and the aqueous phase was completely separated.

(4) Non-Stickiness
Non-stickiness when the sample was applied on the skin was evaluated by 10 professional panelists based on the following criteria. B or greater was regarded as acceptable in the present invention.
  A: 7 or more panelists answered "stickiness was not felt".
  B: 5 or more and 6 or less panelists answered "stickiness was not felt".
  C: 3 or more and 4 or less panelists answered "stickiness was not felt".
  D: 2 or less panelists answered "stickiness was not felt".

TABLE 5

|  |  |  | Examples | | | | | |
|---|---|---|---|---|---|---|---|---|
|  |  |  | 2 | 3 | 4 | 5 | 6 | 7 |
| Formulation | (a) | Cetyl PEG/PPG-10/1 dimethicone | 1 |  |  |  |  |  |
|  |  | Lauryl PEG-9 polydimethylsiloxyethyl dimethicone |  | 1 | 1 | 1 | 1 | 1 |
|  | (c) | Isododecane |  |  |  |  |  | 20 |
|  |  | Cyclopentasiloxane | 20 | 20 | 50 | 80 | 50 |  |
|  | (b) | Core-corona particle (Production example 1) | 1 | 1 | 1 | 1 |  | 1 |
|  |  | Core-corona particle (Production example 2) |  |  |  |  | 1 |  |

TABLE 5-continued

|  |  | Examples | | | | | |
|---|---|---|---|---|---|---|---|
|  |  | 2 | 3 | 4 | 5 | 6 | 7 |
|  | (d) Ethanol | 3.6 | 3.6 | 3.6 | 3.6 | 3.6 | 3.6 |
|  | Purified water | Balance | Balance | Balance | Balance | Balance | Balance |
| Evaluation | Total | 100 | 100 | 100 | 100 | 100 | 100 |
|  | (1) Phase state | W/O | W/O | W/O | W/O | W/O | W/O |
|  | (3) Emulsion particle size (μm) | 1-25 | 1-20 | 1-20 | 1-20 | 1-20 | 1-20 |
|  | (2-1) Emulsification stability (centrifuge treatment) | A | A | A | A | A | A |
|  | (2-2) Emulsification stability (50° C., 4 weeks) | A | A | A | A | A | A |
|  | (4) Non-stickiness | A | A | A | A | A | A |

TABLE 6

|  |  |  | Comparative examples | | | | | | |
|---|---|---|---|---|---|---|---|---|---|
|  |  |  | 3 | 4 | 5 | 6 | 7 | 8 | 9 |
| Formulation | (a) | Polyglyceryl-2 Diisostearate | 1 | 1 |  |  |  |  |  |
|  |  | Distearyldimonium chloride |  |  | 1 | 1 |  |  |  |
|  |  | Sorbitan sesquiisostearate |  |  |  |  | 1 | 1 |  |
|  |  | Amodimethicone |  |  |  |  |  |  | 1 |
|  |  | PEG-10 dimethicone |  |  |  |  |  |  |  |
|  |  | Cetyl PEG/PPG-10/1 dimethicone |  |  |  |  |  |  |  |
|  |  | Lauryl PEG-9 polydimethylsiloxyethyl dimethicone |  |  |  |  |  |  |  |
|  | (c) | Cyclopentasiloxane | 20 | 20 | 20 | 20 | 20 | 20 | 20 |
|  | (b) | Core-corona particle (Production example 2) | 1 |  | 1 |  | 1 |  | 1 |
|  | (d) | Ethanol | 3.6 | 3.6 | 3.6 | 3.6 | 3.6 | 3.6 | 3.6 |
|  |  | Purified water | Balance | Balance | Balance | Balance | Balance | Balance | Balance |
| Evaluation | Total | | 100 | 100 | 100 | 100 | 100 | 100 | 100 |
|  | (1) Phase state | | W/O | W/O | W/O | W/O | W/O | W/O | W/O |
|  | (3) Emulsion particle size (μm) | | 1-10 | 1-10 | 1-10 | 1-10 | 1-10 | 1-10 | 1-15 |
|  | (2-1) Emulsification stability (centrifuge treatment) | | A | B | A | B | A | A | B |
|  | (2-2) Emulsification stability (50° C., 4 weeks) | | B | C | B | C | B | B | C |
|  | (4) Non-stickiness | | A | A | A | A | A | A | A |

|  |  |  | Comparative examples | | | | | |
|---|---|---|---|---|---|---|---|---|
|  |  |  | 10 | 11 | 12 | 13 | 14 | 15 |
| Formulation | (a) | Polyglyceryl-2 Diisostearate |  |  |  |  |  |  |
|  |  | Distearyldimonium chloride |  |  |  |  |  |  |
|  |  | Sorbitan sesquiisostearate |  |  |  |  |  |  |
|  |  | Amodimethicone | 1 |  |  |  |  |  |
|  |  | PEG-10 dimethicone |  | 1 | 1 |  |  |  |
|  |  | Cetyl PEG/PPG-10/1 dimethicone |  |  |  | 1 |  |  |
|  |  | Lauryl PEG-9 polydimethylsiloxyethyl dimethicone |  |  |  |  | 1 | 5 |
|  | (c) | Cyclopentasiloxane | 20 | 20 | 20 | 20 | 20 | 20 |
|  | (b) | Core-corona particle (Production example 2) |  | 1 |  |  |  |  |
|  | (d) | Ethanol | 3.6 | 3.6 | 3.6 | 3.6 | 3.6 | 3.6 |
|  |  | Purified water | Balance | Balance | Balance | Balance | Balance | Balance |
|  | Total | | 100 | 100 | 100 | 100 | 100 | 100 |
| Evaluation | (1) Phase state | | W/O | W/O | W/O | W/O | W/O | W/O |
|  | (3) Emulsion particle size (μm) | | 1-15 | 1-25 | 1-25 | 1-20 | 1-15 | 1-5 |
|  | (2-1) Emulsification stability (centrifuge treatment) | | B | A | B | A | A | A |
|  | (2-2) Emulsification stability (50° C., 4 weeks) | | C | B | B | B | B | A |
|  | (4) Non-stickiness | | A | A | A | A | A | C |

As shown in Table 5, when the polyoxy alkylene/alkyl co-modified silicone type and the core-corona particle were used together as the emulsifier, the water-in-oil emulsion compositions that are significantly excellent in emulsification stability and excellent in non-stickiness were obtained (Examples 2 to 7). These emulsion compositions were resistant against stirring and impact, and were significantly high in temperature stability ((2-1) and (2-2) were all "A").

Moreover, it became significantly stable water-in-oil emulsion systems in a wide range of the oil phase ratio ranging from 20 to 80% by mass (Examples 2 to 7). The core-corona particle is known to produce a good oil-in-water emulsion composition (Patent Literature) even if the ratio of oil-phase/aqueous-phase is high (i.e., the ratio of the oil-phase component in the composition is high); however, it is shown that addition of the polyoxyalkylene/alkyl co-modified silicone surfactant enables to produce a significantly stable water-in-oil emulsion composition in a formulation having a wide range of oil-phase/aqueous-phase ratio (Example 5).

Comparative examples 3 to 12 are compositions prepared with formulations having a non-silicone surfactant (Comparative example 3 to 8), amodimethicone (Comparative examples 9, 10), and PEG-modified silicone (no alkyl modification) (Comparative examples 11, 12) as the surfactant. It became clear from Table 6 that these compositions were low in emulsification stability regardless of presence/absence of the core-corona particle.

Comparative examples 13 and 14 are compositions prepared with formulations in which only the core-corona particle was excluded from the formulations of Examples 2 and 3, respectively. Table 6 shows that, when the compositions of these comparative examples are compared to the compositions of the examples comprising the core-corona particle, there was almost no difference in emulsion particle size and non-stickiness; however, emulsification stability deteriorated remarkably. Furthermore, in the composition in which the blending amount of the polyether-modified silicone (a) was increased up to 5% by mass, emulsification stability improved, but strong stickiness occurred (Comparative example 15).

As stated above, by using the core-corona particle (b) and the polyoxyalkylene/alkyl co-modified silicone (a) in combination as the emulsifier, it is shown that a water-in-oil emulsion composition that is significantly excellent in emulsification stability and also excellent in non-stickiness can be obtained in a formulation having a wide oil-phase/aqueous phase ratio.

What is claimed is:

1. A water-in-oil emulsion composition comprising:
   (a) 0.5 to 3% by mass of a polyoxyalkylene/alkyl co-modified silicone;
   (b) 0.01% by mass or greater of a core-corona particle;
   (c) an oil-phase component; and
   (d) an aqueous-phase component,
   wherein the core-corona particle (b) is obtained by radically polymerizing a polyethylene oxide macromonomer represented by the following formula (1), and a hydrophobic monomer selected from a group consisting of an acrylate/methacrylate derivative monomer represented by the following formula (2) and an acrylamide/methacrylamide derivative monomer represented by the following formula (3), under presence or absence of a crosslinking polymer represented by the following formula (4) and under the following conditions (A) to (E);

(A) a mole ratio expressed by a feed mole amount of the polyethylene oxide macromonomer/a feed mole amount of the hydrophobic monomer is 1:10 to 1:250;
   (B) a feed amount of the crosslinking monomer relative to a feed amount of the hydrophobic monomer is 0.1 to 1.5% by mass;
   (C) the acrylate/methacrylate derivative monomer represented by the following formula (2) has a monomer composition of which one type or two or more types of a methacrylic acid derivative having a 1-8C alkyl group is mixed; and
   the acrylamide/methacrylamide derivative monomer represented by the following formula (3) is an acrylamide derivative or a methacrylamide derivative having a substituent having a 1-18C alkyl group;
   (D) a polymerization solvent is a water-alcohol mixed solvent, and the alcohol is one type or two or more types selected from a group consisting of ethanol, dipropylene glycol, 1,3-butylene glycol and isoprene glycol; and
   (E) solvent composition of the water-alcohol mixed solvent is water:alcohol=90 to 10:10 to 90 in a mass ratio at 20° C.

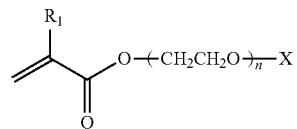

Formula (1)

(1) $R_1$ is a 1-3C alkyl group, and n is a number of 8 to 200, X is H or $CH_3$

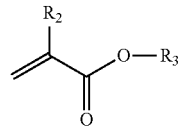

Formula (2)

(2) $R_2$ is a 1-3C alkyl group, and $R_3$ is a 1-12C alkyl group

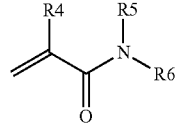

Formula (3)

(3) $R_4$ is H or a 1-3C alkyl group, and $R_5$ and $R_6$ are H or substituents having a 1-18C alkyl group

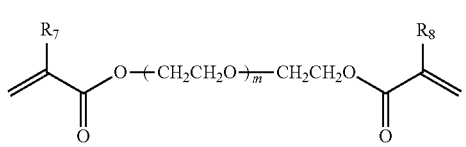

Formula (4)

(4) $R_7$ and $R_8$ are independently a 1-3C alkyl group, and m is a number of 0 to 2.

2. The water-in-oil emulsion composition of claim 1, wherein the component (a) is one type or two or more types of the polyoxyalkylene/alkyl co-modified silicone selected from a group consisting of cetyl PEG/PPG-10/1 dimethicone and lauryl PEG-9 polydimethylsiloxyethyl dimethicone.

3. The water-in-oil emulsion composition of claim 1, wherein 20 to 80% by mass of the oil-phase component (c) is comprised.

4. The water-in-oil emulsion composition of claim 2, wherein 20 to 80% by mass of the oil-phase component (c) is comprised.

* * * * *